United States Patent
Chang et al.

(10) Patent No.: US 8,263,668 B2
(45) Date of Patent: Sep. 11, 2012

(54) TUNABLE FLUORESCENT GOLD NANOCLUSTER AND METHOD FOR FORMING THE SAME

(75) Inventors: Walter Hong-Shong Chang, Taoyuan County (TW); Cherng-Jyh Ke, Taoyuan County (TW); Cheng-An Lin, Taoyuan County (TW); Ching-Yun Chen, Taoyuan County (TW)

(73) Assignee: Chung Yuan Christian University, Taoyuan County (TW)

( * ) Notice: Subject to any disclaimer, the term of this patent is extended or adjusted under 35 U.S.C. 154(b) by 430 days.

(21) Appl. No.: 12/499,550

(22) Filed: Jul. 8, 2009

(65) Prior Publication Data
US 2010/0163806 A1    Jul. 1, 2010

(30) Foreign Application Priority Data
Dec. 31, 2008  (TW) ................ 97151545 A

(51) Int. Cl.
*B01F 3/12*    (2006.01)

(52) U.S. Cl. .......................... 516/33; 977/840
(58) Field of Classification Search .................... 516/33; 977/840
See application file for complete search history.

(56) References Cited

OTHER PUBLICATIONS

Cherng-Jyh Ke, A Novel Method for Direct Synthesis of Fluorescence Gold Nanoclusters, pp. 1-166 (2008).*
Cherng-Jyn Ke, A Novel Method for Direct Synthesis of Fluorescence Gold Nanoclusters, Jul. 24, 2008, p. 1 to 166, Taoyuan County, Taiwan.

* cited by examiner

*Primary Examiner* — Randy Boyer
(74) *Attorney, Agent, or Firm* — WPAT., P.C.; Justin King

(57) ABSTRACT

The present invention discloses a tunable fluorescent gold nanocluster. The tunable fluorescent gold nanocluster is formed by mixing gold trichloride ($AuCl_3$) with toluene solvent without reductant. The tunable fluorescent gold nanocluster emits blue fluorescence that can be red shifted through ultrasonic vibration. The spectral region of the tunable fluorescent gold nanocluster is from 400 nm to 550 nm.

14 Claims, 4 Drawing Sheets

TUNABLE FLUORESCENT GOLD NANOCLUSTER AND METHOD FOR FORMING THE SAME

BACKGROUND OF THE INVENTION

1. Field of the Invention

The present invention is generally related to a fluorescent gold nanocluster, and more particularly to a tunable fluorescent gold nanocluster.

2. Description of the Prior Art

Recently, quantum dots with excellent optical characteristic have successfully overcome the threshold in biological and medical optical probes to become important nano-materials as new generation fluorescent probes. There are great advances and breakthroughs in cellular 3D imaging, long-term living cell monitoring, single-molecule dynamic intracellular tracing, long-term optical sensor fabricating and research, diagnosis and therapy for cancer. Besides, since quantum dots are quickly industrialized and have great business opportunity, they become a very successful role model in nano-biotechnology. Particularly, gold metal fluorescent materials are preferred that have high electron density, high contrast under an electron microscope, and very high biocompatibility and are proven to be successfully applied in various biomedical labeling or optical component fabrication by altering the size of clusters to have different color of fluorescence. However, the fluorescence characteristic of such materials is far inferior to commercially available Cd-based or Pb-based (toxic heavy metal based) water-soluble quantum dots. In addition, due to difficulty in fabrication and mass production as well as time consuming in fabrication, up to now the development in biomedical application is limited. Therefore, it is an important task to develop a fluorescent gold nano-material having the characteristics of being easy to be fabricated, low-cost, having low environmental toxicity and tunable fluorescence.

SUMMARY OF THE INVENTION

In light of the above background, in order to fulfill the industrial requirements, the invention provides a tunable fluorescent gold nanocluster.

The characteristic of the present invention is to provide a tunable fluorescent gold nanocluster and a method for forming the same. The tunable fluorescent gold nanocluster is formed by mixing gold trichloride ($AuCl_3$) with toluene solvent without reductant. The tunable fluorescent gold nanocluster emits blue fluorescence and the spectral region of the nanocluster is from 400 nm to 500 nm where the main peak is at 455 nm while the ultraviolet absorption spectral region of the nanocluster is from 300 nm to 350 nm. Furthermore, the fluorescence spectral region of the tunable fluorescent gold nanocluster is red shifted if the nanocluster is processed by ultrasonic vibration. The tunable fluorescence is from 400 nm to 550 nm.

Accordingly, the present invention discloses a tunable fluorescent gold nanocluster and a method for forming the same. The tunable fluorescent gold nanocluster can be used as a bioprobe to be applied in the application selected from the group consisting of the following: fluorescent biological label, clinical imaging contrast agent and clinical detection, trace and therapy.

DESCRIPTION OF THE PREFERRED EMBODIMENTS

Figure 1:
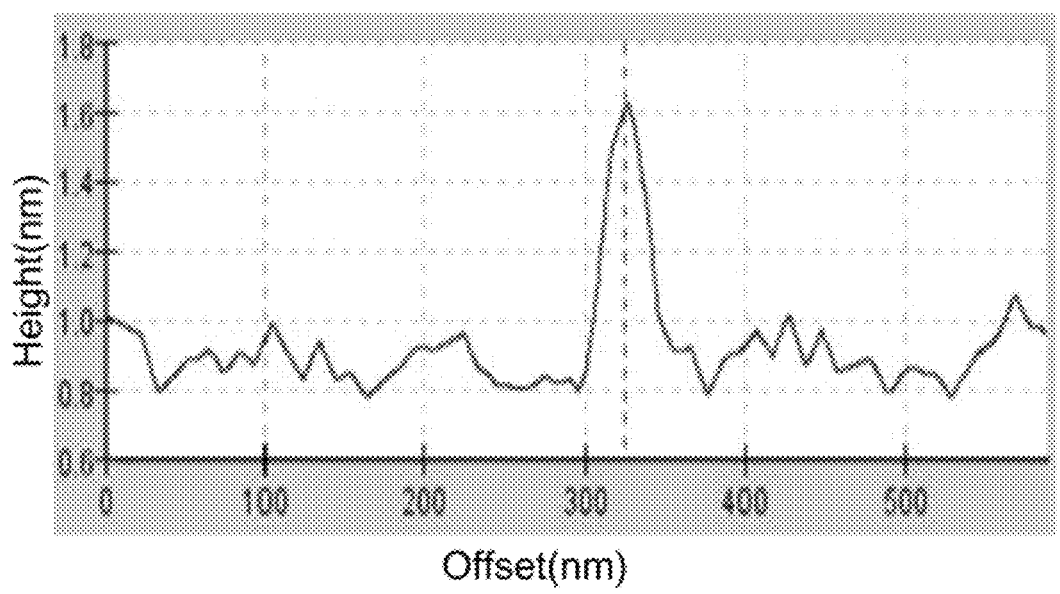
FIG. 1 shows the diameters of tunable fluorescent gold nanocluster from the atomic force microscopic picture according to one embodiment of the invention.

What is probed into the invention is a tunable fluorescent gold nanocluster. Detail descriptions of the structure and elements will be provided in the following in order to make the invention thoroughly understood. Obviously, the application of the invention is not confined to specific details familiar to those who are skilled in the art. On the other hand, the common compositions and steps that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a tunable fluorescent gold nanocluster is provided. The tunable fluorescent gold nanocluster is formed by mixing gold trichloride ($AuCl_3$) with toluene solvent without reductant. The tunable fluorescent gold nanocluster emits blue fluorescence and the spectral region of the tunable fluorescent gold nanocluster is from 400 nm to 500 nm where the main peak is at 455 nm while the ultraviolet absorption spectral region of the nanocluster is from 300 nm to 350 nm. Furthermore, the fluorescence spectral region of the tunable fluorescent gold nanocluster is red shifted if the nanocluster is processed by ultrasonic vibration.

The tunable fluorescence is from 400 nm to 550 nm. Through adjustment and control, the tunable fluorescent gold nanocluster can clearly show blue, green, and yellow fluorescence where the spectral region of green fluorescence is around 425 nm~525 nm and the spectral region of yellow fluorescence is around 450 nm~550 nm.

Moreover, ultrasonic vibration can be used to adjust and control the particle diameter of the tunable fluorescent gold nanocluster. The particle diameter of the nanocluster increases with the increase of the time being processed by ultrasonic vibration. Preferably, the ultrasonic vibration processing time is less than or equal to 180 minutes.

Therefore, from the above description, the tunable fluorescent gold nanocluster can be used as a bioprobe to be applied in the application selected from the group consisting of the following: fluorescent biological label, clinical imaging contrast agent and clinical detection, trace and therapy.

In another embodiment of the present invention, a method for forming a tunable fluorescent gold nanocluster is provided. The method at least comprises forming the tunable fluorescent gold nanocluster by mixing gold trichloride (AuCl$_3$) with toluene solvent without reductant. The tunable fluorescent gold nanocluster emits blue fluorescence and the fluorescence spectral region of the tunable fluorescent gold nanocluster is from 400 nm to 500 nm where the main peak is at 455 nm while the ultraviolet absorption spectral region of the nanocluster is from 300 nm to 350 nm. Furthermore, the fluorescence spectral region of the tunable fluorescent gold nanocluster is red shifted if the nanocluster is processed by ultrasonic vibration.

The tunable fluorescence is from 400 nm to 550 nm. Through adjustment and control, the tunable fluorescent gold nanocluster can clearly show blue, green, and yellow fluorescence where the spectral region of green fluorescence is around 425 nm~525 nm and the spectral region of yellow fluorescence is around 450 nm~550 nm.

Moreover, ultrasonic vibration can be used to adjust and control the particle diameter of the tunable fluorescent gold nanocluster. The particle diameter of the nanocluster increases with the increase of the time being processed by ultrasonic vibration. Preferably, the ultrasonic vibration processing time is less than or equal to 180 minutes.

In one preferred example of this embodiment, the method further comprises performing a centrifugal procedure on the mixture of gold trichloride (AuCl$_3$) and toluene to separate out the tunable fluorescent gold nanocluster having a specific fluorescence spectrum.

In another preferred example of this embodiment, the method further comprises performing ultraviolet radiation on the tunable fluorescent gold nanocluster having a specific fluorescence spectrum to have the specific fluorescence spectrum change from a single peak to double peaks. In addition, the particle diameter of the tunable fluorescent gold nanocluster increases after ultraviolet radiation.

To sum up, from the above description, the tunable fluorescent gold nanocluster can be used as a bioprobe to be applied in the application selected from the group consisting of the following: fluorescent biological label, clinical imaging contrast agent and clinical detection, trace and therapy.

EXAMPLE 1

Fluorescent Gold Nanocluster (1) Preparation of Tunable Fluorescent Gold Nanoclusters At first, 0.03 g of gold trichloride (AuCl$_3$) is weighted and placed in an 8-mL glass specimen bottle. Then, 4 mL of toluene (HPLC grade) is added in the bottle and the bottle is placed on a vibrator for 3 minutes of vibration. A deep brown muddy solution is thus obtained. The muddy solution is then placed in a centrifuge and processed by 4000 rpm for 5 minutes. Then, an upper clarified brown solution is obtained and the preparation of tunable fluorescent gold nanoclusters is complete. FIG. 1 shows the average particle diameter of the nanoclusters is 1.6 nm, calculated from the atomic force microscopic picture. The clarified brown solution is preserved at 4° C. in an 8-mL glass specimen bottle.

(2) Ultrasonic Vibration on Tunable Fluorescent Gold Nanoclusters

The tunable fluorescent gold nanoclusters prepared in the above section (1) are taken and the specimen is mounted on a test tube rack and placed in a ultrasonic vibrator (40 KHz, 30 W) containing 5 L of water. The water level of the ultrasonic vibrator is higher than that of the fluorescent gold nanocluster solution.

Figure 2A:
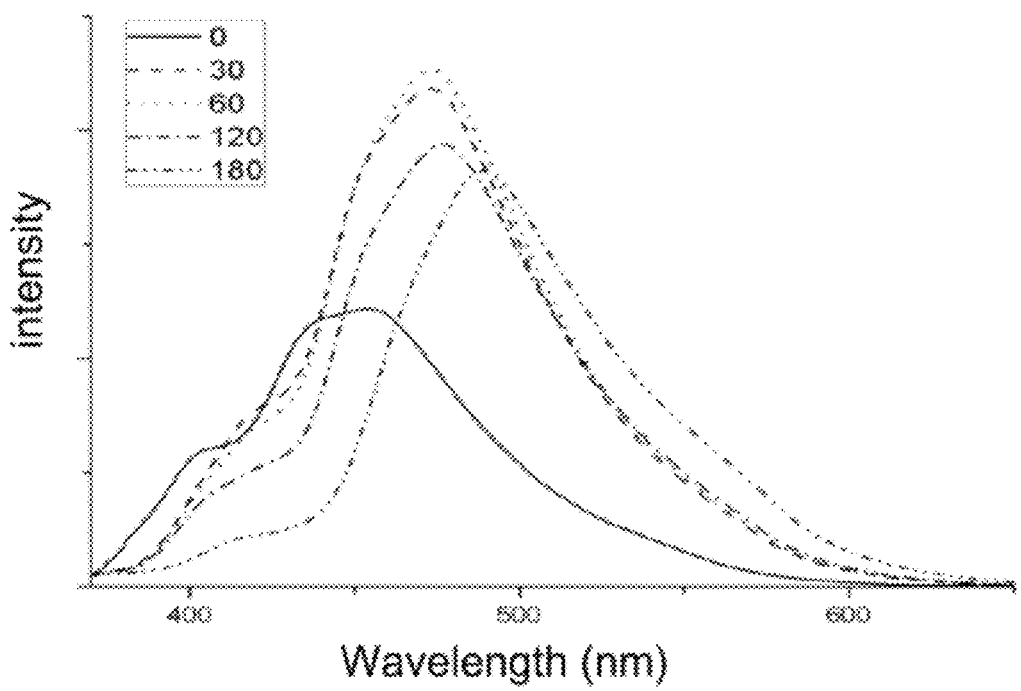
FIGS. 2A and 2B show fluorescence spectra of the tunable fluorescent gold nanocluster after processed by ultrasonic vibration according to one embodiment of the present invention.
Figure 2B:
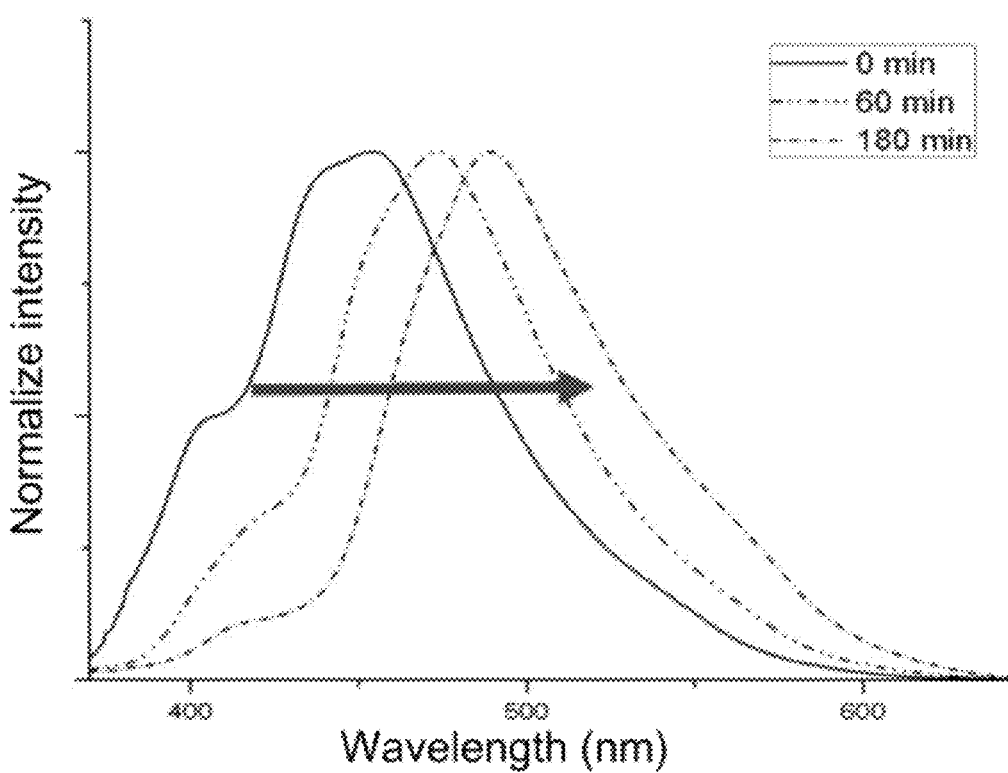

The processing time by the ultrasonic vibrator is: 0, 30, 60, 120, and 180 minutes, separately. After processed by the ultrasonic vibrator, it is processed by a centrifuge with 4000 rpm for 5 minutes and then an upper clarified solution is obtained. The color of the tunable fluorescent gold nanocluster solution becomes darker if the processing time by the ultrasonic vibrator is longer. In addition, the specific fluorescence spectral region of the gold nanocluster is red shifted after the gold nanocluster is processed by ultrasonic vibration. The fluorescence of the nanocluster changes from blue to green and then to yellow while continuing processed by ultrasonic vibration. The fluorescence spectra are shown in FIGS. 2A and 2B.

(3) Ultraviolet Radiation on Tunable Fluorescent Gold Nanoclusters

Figure 3:
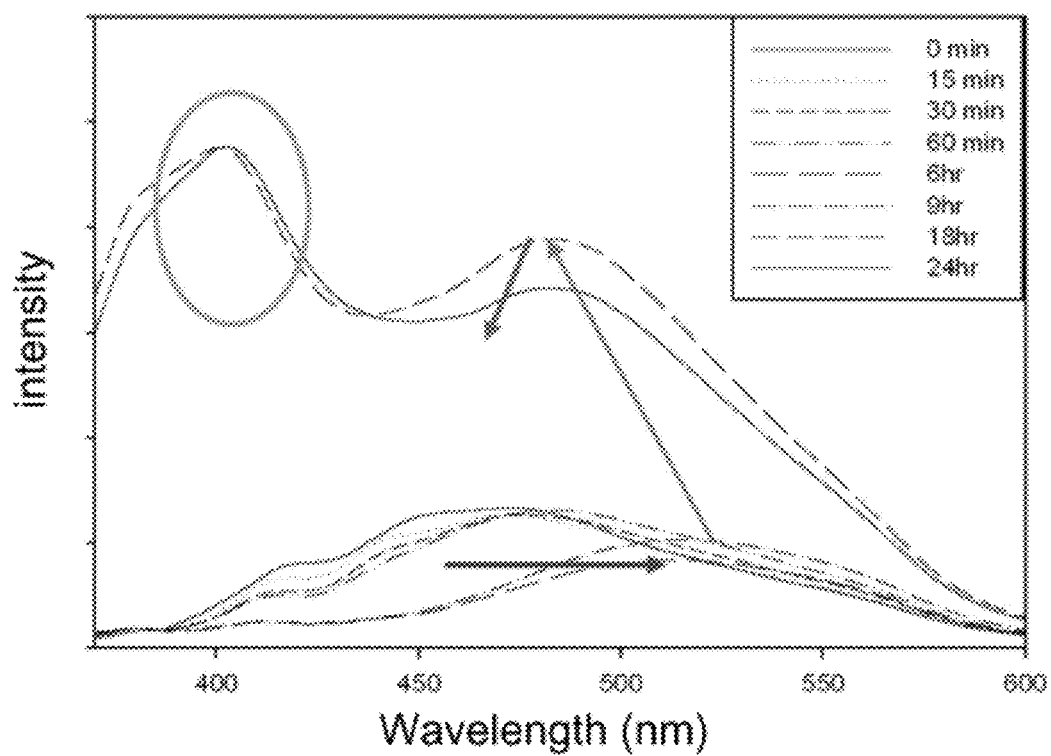
FIG. 3 shows a fluorescence spectrum of the tunable fluorescent gold nanocluster after ultraviolet radiation according to one embodiment of the present invention.

As shown in FIG. 3, the tunable fluorescent gold nanoclusters are processed by ultraviolet radiation. The time for ultraviolet radiation is 0 min, 15 min, 30 min, 60 min, 6 hrs, 9 hrs, 18 hrs, and 24 hrs, separately.

There is no apparent change after processed by ultraviolet radiation within 1 hour. As the radiation time lasts for 6~9 hours, the fluorescence of the nanocluster is red shifted but the fluorescence intensity has no apparent change. However, after continuing ultraviolet radiation for 18 hours, the fluorescence intensity of the nanocluster increases significantly. Besides, the fluorescence spectrum changes from a single peak to double peaks. The double peaks are centered at 410 nm and 470 nm, separately.

(4) Particle Diameter of Tunable Fluorescent Gold Nanoclusters

Figure 4:
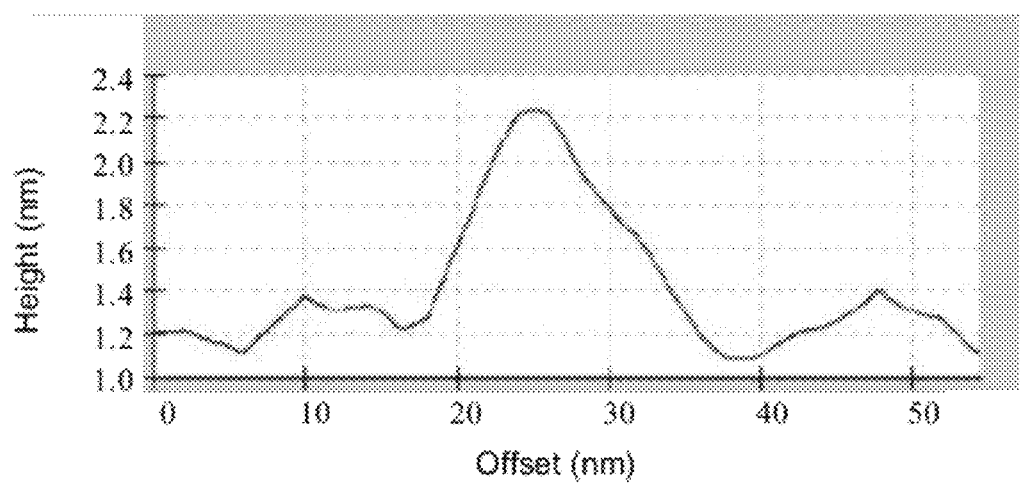
FIG. 4 shows the diameter and the height of the tunable fluorescent gold nanocluster after 24-hour ultraviolet radiation according to one embodiment of the present invention.
Figure 5:
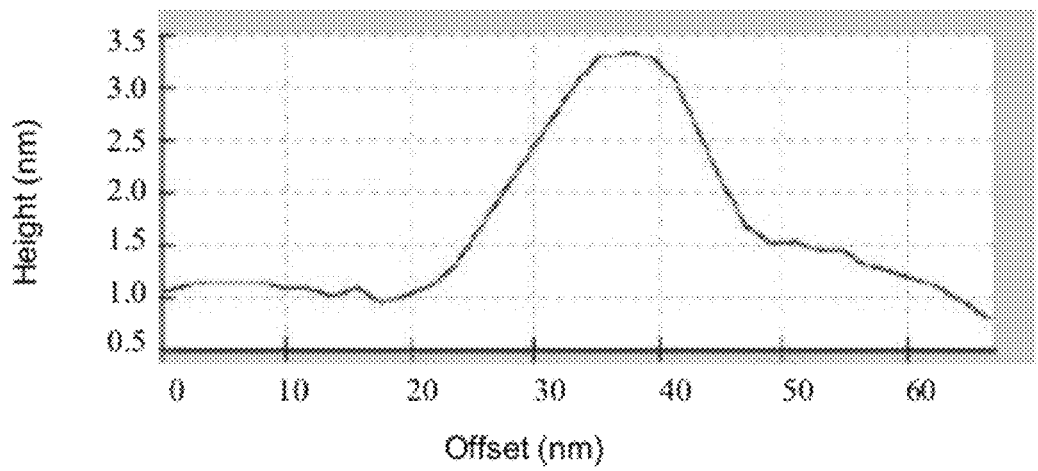
FIG. 5 shows the diameter and the height of the tunable fluorescent gold nanocluster after 60-minute ultrasonic vibration and 24-hour ultraviolet radiation according to one embodiment of the present invention.

From the above sections (2) and (3), after the tunable fluorescent gold nanoclusters are processed by (2) ultrasonic vibration or (3) ultraviolet radiation, the fluorescence spectral region of the nanoclusters is red shifted. According to quantum confinement effect, as the particle diameter is larger, the fluorescence spectral region is red shifted. Thus, the particle diameter of the tunable fluorescent gold nanoclusters can be controlled by ultrasonic vibration or ultraviolet radiation. The particle diameter of the tunable fluorescent gold nanocluster increases with the increase of the processing time by ultrasonic vibration. In addition, the particle diameter of the tunable fluorescent gold nanocluster increases with the increase of the processing time by ultraviolet radiation, as shown in FIGS. 4 and 5.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for forming a tunable fluorescent gold nanocluster, at least comprising: forming the tunable fluorescent gold nanocluster by mixing gold trichloride (AuCl$_3$) with toluene solvent without reductant.

2. The method according to claim 1, further comprising: performing a centrifugal procedure on the mixture of gold trichloride (AuCl$_3$) and toluene to separate out the tunable fluorescent gold nanocluster having a specific fluorescence spectrum.

3. The method according to claim 1, wherein the fluorescence spectral region of the tunable fluorescent gold nanocluster is from 400 nm to 500 nm.

4. The method according to claim 1, further comprising: performing ultrasonic vibration on the tunable fluorescent gold nanocluster having a specific fluorescence spectrum to have the specific fluorescence spectral region red-shifted.

5. The method according to claim 4, wherein the fluorescence spectral region of the tunable fluorescent gold nanocluster is from 450 nm to 550 nm.

6. The method according to claim 4, wherein the fluorescence spectral region of the tunable fluorescent gold nanocluster after ultrasonic vibration is from 425 nm to 525 nm.

7. The method according to claim 4, wherein the fluorescence spectral region of the tunable fluorescent gold nanocluster after ultrasonic vibration is from 450 nm to 550 nm.

8. The method according to claim 1, wherein ultrasonic vibration is used to adjust and control the particle diameter of the nanocluster.

9. The method according to claim 8, wherein the particle diameter of the nanocluster increases as the time of being processed by ultrasonic vibration increases.

10. The method according to claim 4, wherein the time of being processed by ultrasonic vibration is less than or equal to 180 minutes.

11. The method according to claim 1, further comprising: performing ultraviolet radiation on the tunable fluorescent gold nanocluster having a specific fluorescence spectrum to have the specific fluorescence spectrum change from a single peak to double peaks.

12. The method according to claim 1, wherein the ultraviolet absorption spectral region of the tunable fluorescent gold nanocluster is from 300 nm to 350 nm.

13. The method according to claim 11, wherein the particle diameter of the nanocluster increases after ultraviolet radiation.

14. The method according to claim 1, wherein the nanocluster is used as a bioprobe applied in the application selected from the group consisting of the following: fluorescent biological label, clinical imaging contrast agent and clinical detection, trace and therapy.

* * * * *